United States Patent
Ebanks et al.

(10) Patent No.: US 11,065,192 B2
(45) Date of Patent: Jul. 20, 2021

(54) MASCARA COMPOSITIONS INCLUDING VINYLPYRROLIDONE HOMOPOLYMER AND AN ACRYLIC FILM-FORMING POLYMER

(71) Applicant: L'OREAL, Paris (FR)

(72) Inventors: Jody Ebanks, Bloomfield, NJ (US); Christopher Pang, New York, NY (US); Christopher Michael MacNeill, Fanwood, NJ (US); Tsang-Min Huang, Scotch Plains, NJ (US)

(73) Assignee: L'OREAL, Paris (FR)

( * ) Notice: Subject to any disclaimer, the term of this patent is extended or adjusted under 35 U.S.C. 154(b) by 0 days.

(21) Appl. No.: 15/825,934

(22) Filed: Nov. 29, 2017

(65) Prior Publication Data
US 2019/0159995 A1 May 30, 2019

(51) Int. Cl.
*A61K 8/81* (2006.01)
*A61Q 1/10* (2006.01)

(52) U.S. Cl.
CPC .......... *A61K 8/8176* (2013.01); *A61K 8/8147* (2013.01); *A61K 8/8152* (2013.01); *A61Q 1/10* (2013.01)

(58) Field of Classification Search
CPC .............. A61K 8/8176; A61K 2800/10; A61K 8/8152; A61Q 1/10
See application file for complete search history.

(56) References Cited

U.S. PATENT DOCUMENTS

| | | | |
|---|---|---|---|
| 6,517,823 B1 | 2/2003 | Norman et al. | |
| 7,504,093 B2 | 3/2009 | Bracken et al. | |
| 2003/0068290 A1* | 4/2003 | Auguste | A61K 8/044 424/70.11 |
| 2006/0030655 A1* | 2/2006 | L'Alloret | A61K 8/062 524/315 |
| 2007/0081964 A1* | 4/2007 | Muller | A61K 8/046 424/70.15 |
| 2017/0035679 A1 | 2/2017 | Douezan et al. | |
| 2017/0065512 A1 | 3/2017 | Zhu et al. | |

FOREIGN PATENT DOCUMENTS

| | | | |
|---|---|---|---|
| JP | 2009046517 A | * | 3/2009 |
| WO | 2010014328 A2 | | 2/2010 |
| WO | 2017044546 A1 | | 3/2017 |

OTHER PUBLICATIONS

JP 2009046517 A, English translation from Espacenet, downloaded Feb. 2020 (Year: 2020).*
"Waterproof Eyebrow Mascara," Mintel GNPD, record ID 3650969, published Dec. 2015, p. 1-3.
Dr. Claudia Wood, Dr. Peter Hoessel, Luviset Clear—a New Styling Polymer for Crystal Clear Hair Gels, Cosmetic Science and Technology, 2004, p. 112, BASF, Germany.

* cited by examiner

*Primary Examiner* — Mark V Stevens
(74) *Attorney, Agent, or Firm* — Oblon, McClelland, Maier & Neustadt, L.L.P.

(57) ABSTRACT

A mascara composition includes a film-forming polymer portion. The film-forming polymer portion is stabilized in a vehicle that includes water. The film-forming polymer portion includes a high molecular weight vinylpyrrolidone homopolymer and an acrylic polymer having a glass transition temperature of 65° C. or more. The mascara composition includes at least about 10 percent by weight of the vinylpyrrolidone homopolymer and is substantially free of wax. Methods of applying makeup to the eyelashes are also provided.

17 Claims, No Drawings

MASCARA COMPOSITIONS INCLUDING VINYLPYRROLIDONE HOMOPOLYMER AND AN ACRYLIC FILM-FORMING POLYMER

FIELD OF THE INVENTION

The present invention relates to a cosmetic composition for keratinous materials such as keratin fibers. The cosmetic composition is preferably a mascara composition for eyelashes.

DISCUSSION OF THE BACKGROUND

Mascara compositions are commonly used to enhance the appearance of eyelashes. Conventional mascara compositions generally use waxes to form crystalline network structures to enhance curl, volume, length, thickness, and/or colors to eyelashes. However, mascara compositions including large amount of waxes tend to become less resistant to oil and/or sebum, causing smearing, flaking, and/or color transferring after wearing for a certain amount of time. Furthermore, while conventional high wax mascara can be used to assist in moderate curl formation eyelashes, users of mascara typically are forced to rely on particular applicators or eye-lash curling devices to enhance curl to any substantial degree.

The inventors of the present have found that certain mascara formulations with little or no wax are actually useful for inducing a curling effect and lastingness to eyelashes as compared to conventional mascara formulations.

Accordingly, one aspect of the present invention is a mascara composition which is able to impart an enhanced appearance to the eyelashes by enhancing eyelash curling. Another aspect of the present invention is directed to a method of making up eyelashes to enhance physical appearance of the eyelashes.

SUMMARY OF THE INVENTION

According to certain embodiments of the present invention, a mascara composition includes a film-forming polymer portion. The film-forming polymer portion is stabilized in a vehicle that includes water. The film-forming polymer portion includes a high molecular weight vinylpyrrolidone homopolymer and an acrylic polymer having a glass transition temperature of about 65° C. or more. The mascara composition includes at least about 10 percent by weight of the vinylpyrrolidone homopolymer and is substantially free of wax.

According to other aspects of the present invention, a method of applying makeup to the eyelashes. The method includes applying to a top surface of eyelashes a mascara composition that includes a film-forming polymer portion. The film-forming polymer portion is stabilized in a vehicle that includes water. The film-forming polymer portion includes a high molecular weight vinylpyrrolidone homopolymer and an acrylic polymer having a glass transition temperature of about 65° C. or more. The mascara composition includes at least about 10 percent by weight of the vinylpyrrolidone homopolymer and is substantially free of wax.

It is to be understood that both the foregoing general description and the following detailed description are exemplary and explanatory only, and are not restrictive of the invention.

DETAILED DESCRIPTION OF THE INVENTION

Unless otherwise indicated, all numbers expressing quantities of ingredients and/or reaction conditions are to be understood as being modified in all instances by the term "about." Accordingly, unless indicated to the contrary, the numerical parameters set forth in the following specification and attached claims are approximations that may vary depending upon the desired properties sought to be obtained by the present invention.

As used herein, the expression "at least one" means one or more and thus includes individual components as well as mixtures/combinations.

Other than in the operating examples, or where otherwise indicated, all numbers expressing quantities of ingredients and/or reaction conditions are to be understood as being modified in all instances by the term "about," meaning within 10% to 15% of the indicated number.

As used herein, "mascara" and "mascara composition" mean a composition that is intended to be applied to keratinous materials, preferably keratin fibers, in particular eyelashes and/or eyebrows, further in particular eyelashes.

As used herein, "keratinous materials" include, but are not limited to, skin, nail, living keratin fibers such as head hair, eyelashes, and eyebrows, and non-living keratin fibers such as swatches, extensions, and false eyelashes. The living and non-living keratin fibers include any mammalian hair, including human hair.

"Percent" or "%" as used herein, when referring to concentrations of ingredients or components in compositions refers to percent by weight. Unless otherwise stated, the percent is relative to the entire mascara composition.

"Solids basis" or "actives basis" refers to the amount of a particular ingredient exclusive of any solvents, carriers, impurities and the like that may be supplied with the particular ingredient "Substantially free" as used herein to refer to the presence of ingredients within compositions of the present invention, means that the particular ingredient is present in concentrations by weight of less than about 1%, such as less than about 0.5%, such as less than about 0.25%, such as about 0%.

"Substituted" as used herein, means comprising at least one substituent. Non-limiting examples of substituents for substitution include atoms, such as oxygen atoms and nitrogen atoms, as well as functional groups, such as hydroxyl groups, ether groups, alkoxy groups, acyloxyalky groups, oxyalkylene groups, polyoxyalkylene groups, carboxylic acid groups, amine groups, acylamino groups, amide groups, halogen containing groups, ester groups, thiol groups, sulphonate groups, thiosulphate groups, siloxane groups, and polysiloxane groups. The substituent(s) may be further substituted.

The term "self-curling" refers to an attribute associate with compositions of the present invention. Self-curling refers to the ability of a composition to induce curling on eyelashes upon drying—and not from use of an applicator that is specifically to induce curling. Self-curling may be measured using the SELF CURLING TEST noted in this specification.

Mascara Composition

According to the present invention, the inventors have found that particular mascara compositions of the present invention have surprising and unexpected properties such as those related to self-curling. These compositions include a film-forming polymer portion that includes a high molecular weight vinylpyrrolidone homopolymer and one or more secondary film-forming polymers each having one or more repeat units that include imide functionality and/or acid anhydride functionality. The mascara composition comprises at least about 10 percent by weight of the vinylpyrrolidone homopolymer on a solids basis and is substantially free of wax.

Film-Forming Polymer Portion

Mascara compositions of the present invention include a film-forming polymer portion. The film-forming polymer portion includes one or more film-forming polymers. One of ordinary skill in the art will readily appreciate the term "film-forming polymer" refers or "film forming agent" as used herein means a polymer or resin that leaves a film (e.g., a continuous film) on the substrate to which it is applied, for example, after a solvent accompanying the film former has evaporated, absorbed into and/or dissipated on or from the substrate. In order to evaluate whether a polymer is a film forming polymer a drawdown test may be performed by putting 5 to 10 grams of material on the center of a Leneta card stock (Black and White Opacity card Chart 2812 available from BYK Additives and Instruments of Geretsried, Germany) and using a 3 mil Drawdown Birdbar (also from Byk), spreading the material for across the sheet (8 in by 3 in) and allowing it to dry overnight. If the material forms a conformal coating and/or can picked up or scraped off with a razorblade to be removed as a free standing film, then it is film forming. Regardless, if it does not coat the card, cannot in any reasonable way be removed as a freestanding film and/or forms a loose powdery coating that rubs off readily onto one's finger, then it is not a film former. Film-forming polymers that are cosmetically or dermatologically acceptable may be utilized in the present invention. As used herein, "cosmetically acceptable" or "dermatologically acceptable" is intended to mean that a composition is suitable for use in contact with human tissues such as keratinous materials and mucous membranes without undue toxicity, incompatibility, instability, and/or allergic response.

The film forming polymer portion includes a vinylpyrrolidone homopolymer. Vinylpyrrolidone homopolymers (also known as polyvinylpyrrolidone) are water soluble polymers chemically composed of repeating 5-membered heterocyclic rings i.e., $C_6H_9NO$ units. Vinylpyrrolidone homopolymers useful in the present invention are high molecular weight. By "high molecular weight" it is meant having a weight average molecular weight ($M_w$) that is at least about 200,000 daltons. In certain embodiments of the invention the $M_w$ of the vinylpyrrolidone homopolymer is at least about 350,000 daltons. According to certain other embodiments of the invention, in order to enhance self-curling and assist in the ease of application to lashes, the vinylpyrrolidone homopolymer has an $M_w$ that is from about 200,000 daltons to about 3,000,000 daltons such as from about 500,000 daltons to about 1,500,000 daltons.

In certain embodiments, the high molecular weight vinylpyrrolidone homopolymer may be a commercially available variety, such as PVP K-60 (or Plasdone® K-60), PVPK-90 (or Plasdone® K-90), or PVP K-120 (or Plasdone® K-120), each commercially available from Ashland, Inc of Kovington, Ky.

The concentration of the high molecular weight vinylpyrrolidone homopolymer in the mascara is greater than about 10%. In certain embodiments the concentration of the high molecular weight vinylpyrrolidone homopolymer is greater than about 15%. According to certain other embodiments the concentration of the high molecular weight vinylpyrrolidone homopolymer is from about 10%, 15%, or 20% to about 25%, 30% or 40% including all combinations of such ranges, relative to the total weight of the mascara composition.

The film-forming polymer portion also includes an acrylic polymer that has a glass transition temperature of about 65° C. or more, and, in certain embodiments of the invention, 90° C. or more. As one skilled in the art will recognize, glass transition temperature, $T_g$, may be measured using, for example, differential scanning calorimetry such as using a heating and cooling rate of 10 degrees/minute. Furthermore, as one skilled in the art will recognize, by the term "acrylic polymer" it is meant a polymer derived from any number of ethylenically unsaturated monomers including, but not limited to those monomers selected from acrylic acid; methyl, ethyl and other alkyl (meth)acrylates; including crosslinked and uncrosslinked acrylate polymers. In certain embodiments, the acrylic polymer includes one or more monomers selected from a group consisting of acrylic acid, methacrylic acid, acrylamide, methacrylamide, alkyl acrylates, alkyl methacrylates, and styrene. In certain other embodiments, the acrylic polymer consists of one or more monomers selected from a group consisting of acrylic acid, methacrylic acid, alkyl acrylates, and alkyl methacrylates.

In certain embodiments, the acrylic polymer is ionic, and in certain notable embodiments, anionic, such as those anionic acrylic polymers that are supplied as a latex dispersion.

Suitable non-limiting example of acrylate polymers having a glass transition temperature of 65° C. or more include certain copolymers of methacrylic acid/ethyl acrylate such as LUVIMER MAE and LUVIFLEX Soft (INCI: Acrylates Copolymer); certain acrylate/methacrylamide copolymers such as LUVISET One (having INCI designation Acrylates Methacrylamide Copolymers); and certain copolymers of methyl methacrylate/methacrylic acid/urethane acrylate such as LUVISET SHAPE (INCI designation Polyacrylate-22). LUVIMER MAE, LUVIFLEX Soft, LUVISET One, and LUVISET SHAPE are commercially available by BASF Corporation. Examples of other suitable polymers include alkyl(meth)acrylate/(meth)acrylic acid, such as FIXATE Superhold (INCI designation Poylacrylate-2 Crosspolymer) commercially available from Lubrizol Corporation of Wickliffe, Ohio.

The concentration of the acrylate polymers having a glass transition temperature of 65° C. or more in the mascara may from about 5%, 10% or 15% by weight to about 25%, 30% or 40% by weight, including all combinations of such ranges, relative to the total weight of the mascara composition.

In certain embodiments of the invention, the film-forming polymer portion may include yet additional film-forming polymers that may be stabilized in the vehicle. Suitable additional film-forming polymers include, for example, any of various acrylate and acrylic co-polymers, urethane polymers, polyesters and the like that are commonly used in mascara formulations.

According to certain embodiments, the sum of the concentrations of the high molecular weight vinylpyrrolidone polymer and the acrylate polymers having a glass transition temperature of 65° C. or more is 75% or more, such as 90% percent or more by weight of the film-forming polymer portion. According to certain other embodiments, the sum of the primary film-forming polymer and one or more secondary film-forming polymers comprises 95% or more of the film-forming polymer portion, such as about 100% of the film-forming polymer portion.

Wax

Compositions of the present invention are substantially free of wax. As used herein, "wax" is intended to mean a lipophilic fatty compound that is solid at room temperature (about 25° C.) and atmospheric pressure (760 mmHg, i.e., 105 Pa), which undergoes a reversible solid/liquid change of state and which has a melting point of greater than 30° C., and in some embodiments, greater than about 55° C. up to about 120° C. or even as high as about 200° C.

The term wax may include waxes of animal origin, waxes of plant origin, waxes of mineral origin and waxes of synthetic origin. Examples of waxes of animal origin include beeswaxes, lanolin waxes and Chinese insect waxes. Examples of waxes of plant origin include rice waxes, carnauba wax, candelilla wax, ouricurry wax, cork fiber waxes, sugar cane waxes, Japan waxes, sumach wax and cotton wax. Examples of waxes of mineral origin include paraffins, microcrystalline waxes, montan waxes and ozokerites. Examples of waxes of synthetic origin include polyolefin waxes, e.g., polyethylene waxes, waxes obtained by Fischer-Tropsch synthesis, waxy copolymers and their esters, and silicone and fluoro waxes.

The term wax may further include high melting point hydrogenated oils of animal or plant origin. Examples include hydrogenated jojoba waxes and hydrogenated oils which are obtained by catalytic hydrogenation of fats composed of a $C_8$-$C_{32}$ linear or nonlinear fatty chain, hydrogenated sunflower oil, hydrogenated castor oil, hydrogenated copra oil, hydrogenated lanolin and hydrogenated palm oils.

Oil

Compositions of the present invention may additionally be substantially free of oils. In certain particular embodiments, compositions of the present invention have less than 0.25% of waxes and less than 0.25% of oils.

As used herein, by "oils," it is meant compounds having a melting point of less than about 30 C and generally insoluble in water and includes a hydrophobic moiety, such as one meeting one or more of the following three criteria: (a) has a carbon chain of at least six carbons in which none of the six carbons is a carbonyl carbon or has a hydrophilic moiety (defined below) bonded directly to it; (b) has two or more alkyl siloxy groups; or (c) has two or more oxypropylene groups in sequence. The hydrophobic moiety may include linear, cyclic, aromatic, saturated or unsaturated groups. The hydrophobic compound is in certain embodiments not amphiphilic and, as such, in this embodiment does not include hydrophilic moieties, such as anionic, cationic, zwitterionic, or nonionic groups, that are polar, including sulfate, sulfonate, carboxylate, phosphate, phosphonate, ammonium, including mono-, di-, and trialkylammonium species, pyridinium, imidazolinium, amidinium, poly(ethyleneiminium), ammonioalkylsulfonate, ammonioalkylcarboxylate, amphoacetate, and poly(ethyleneoxy)sulfonyl moieties. In certain embodiments, the oil does not include hydroxyl moieties.

Suitable examples of compounds of oils include vegetable oils (glyceryl esters of fatty acids, triglycerides) and fatty esters. Specific non-limiting examples include, without limitation, esters such as isopropyl palmitate, isopropyl myristate, isononyl isonanoate $C_{12}$-$C_{15}$ alkyl benzoates, caprylic/capric triglycerides, silicone oils (such as dimethicone and cyclopentasiloxane), pentaerythritol tetraoctanoate and mineral oil. Other examples of oils include liquid organic ultraviolet filter commonly used for example as UV-absorbing sunscreens such as octocrylene, octyl salicylate, octyl methoxycinnamate, among others.

Surfactants and Dispersants

The film-forming polymer may provide sufficient thickening of the vehicle to obviate the need for dispersants or suspending agents. However, according to certain embodiments of the present invention, the mascara composition may further optionally include a surfactant or dispersant, primarily to assist in wetting or dispersing of the particulate portion. Any surfactants, including anionic, non-ionic, amphoteric, and cationic, surfactants, may be used in the present invention, as long as the surfactant is cosmetically or dermatologically acceptable. The surfactant may be used either singly or in combination two or more thereof. In one embodiment, the mascara composition may include an anionic surfactant/dispersant such as sodium laureth sulfate.

If present, the amount of the surfactant or dispersant may be from about 0.1 to about 5% by weight. In certain other embodiments the concentration of dispersants and surfactants is limited to less than 1%, such as less than about 0.5%, such as less than about 0.1%.

Colorants and Particulates

Mascara compositions of the present invention may optionally include at least one colorant. Suitable colorants include, but are not limited to inorganic particulates that impart color or optical effects and organic pigments. Particulate materials are generally finely divided particulates that are insoluble in but are otherwise homogeneously stabilized (suspended or dispersed) in a vehicle of the composition. The one or more particulate materials are typically materials that are incapable of chemically "self-fusing" in-use and are not themselves film-forming.

Suitable inorganic particulate materials include any of a variety of porous, semi-porous, non-porous, or hollow, coated or uncoated water-insoluble inorganic particulates such as silica, alumina, carbon and any of various oxides, silicates, aluminosilicates, nitrides, carbides, carbonates, and the like. In particular embodiments, the inorganic particulate is selected from carbon black, silica, and iron oxide. Other particulates, e.g., organic pigments such as lake pigments; other organic particulates such as polymeric particulates including nylon particulates, acrylate particulates (e.g., PMMA), silicone elastomer particulates, and the like may also be used.

Any of various lipophilic or water soluble dyes may be used as well. Typically, when the composition contains colorants, the composition may be used as a mascara composition. Alternatively, when the composition does not contain colorants, it is a clear or transparent composition which can be used as a basecoat (or topcoat) prior to (or after) application of a mascara composition to keratinous materials. A composition free of colorants may also be used as a solitary coating (without an additional separate basecoat or topcoat). However, it is possible that topcoats or basecoats could contain colorants, and/or that a mascara composition could contain little or no colorant.

Vehicle

In order to facilitate application to the eyelashes, mascaras of the present invention generally include a vehicle in which the film-forming polymer portion is stabilized (i.e., dissolved, dispersed or suspended). The vehicle generally includes, consists or consists essentially of water. In certain embodiments of the invention, the mascara compositions of the present invention include at least about 30% water, such as from about 40% to about 90%, such as from about 45% to about 85%.

Additional Ingredients

The mascara composition of the present invention may further include various additives desirably used in cosmetic or dermatological compositions. For example, water, dispersants, anti-oxidants, pH adjusters, preservatives, neutralizing agents, fragrances, fillers, co-solvents, plasticizers, cosmetic and dermatological active agents such as emollients, moisturizers, vitamins, UV filters, and sunscreens, and mixtures thereof can be added. A non-exhaustive listing of such ingredients can be found in the CTFA *International Cosmetic Ingredient Dictionary and Handbook*, Fourteenth Edition (2012), contents of which are incorporated herein by reference in its entirety.

One skilled in the art will take care to select the optional additional additives and/or the amount thereof such that the advantageous properties of the mascara compositions according to the present invention are not, or are not substantially, adversely affected by the envisaged addition.

These substances may be selected variously by one skilled in the art to prepare a composition which has the desired properties, for example, consistency or texture.

According to certain embodiments mascaras of the present invention are substantially free of polyhydric alcohols such as glycerin or glycols such as propylene, butylene or hexylene glycol.

According to certain embodiments, the mascara composition of the present invention is in the form of a water dispersion where the vinylpyrrolidone homopolymer and one or more other ingredients is present as dissolved in the water phase and inorganic particulate and one or more other ingredients is dispersed within the water phase. In other embodiments, the mascara composition may be an emulsion.

According to certain embodiments mascara compositions of the present invention have a viscosity from about 0.01 kPa·s, 0.1 kPa·s or 0.3 kPa·s to about 0.6 kPa·s, 10 kPa·s or 50 kPa·s including all combinations of such ranges, when measured at a shear rate of 1 s$^{-1}$ as measured using, for example, the AR-G2 magnetic bearing rheometer, available from TA Instruments of New Castle, Del. In order to adjust the viscosity of the mascara formulation, one may use one or more viscosity modifiers. According to certain other embodiments of the invention, the mascara may have a pH that is from about 5 to about 8. In certain cases it may be useful to add a viscosity reducing agent such as a C2-C5 alcohol (such as ethanol or isopropyl alcohol) or various salts or electrolytes. In certain embodiments of the invention, if a C2-C5 alcohol is chosen, the concentration of is less than 5%, such as from about 0.25% to about 2%.

According to certain embodiments of the invention, the mascara may have a pH that is from about 5 to about 8.

The mascara composition of the present invention is intended to be applied onto keratinous materials such as keratin fibers, in particular, eyelashes or eyebrows. In certain notable embodiments the mascara is applied to a portion of keratinous surface that one desires to adopt a concave curvature. In particular, the inventors have found that compositions of the present invention are useful for self-curling. When used in this regard, the mascara is applied to the top surface of the upper eyelash and allowed to dry. By applying only to the top surface of the lashes, the lash will curl upwards upon drying.

As described above, according to one aspect of the present invention, the mascara composition has improved cosmetic properties such as, for example, increased volume properties, increased self-curling properties, increased self-curl retention properties, increased length properties, and the like.

Methods

Mascara compositions of the present invention may be made by mixing at least one vinylpyrrolidone homopolymer in water until dissolution. The vinylpyrrolidone homopolymer and other water-soluble ingredients may be mixed by stirring, shaking, grounding, or beating, optionally with a stirrer, a magnetic stirrer, a shaker, a homogenizer, or any other methods suitably used to mix cosmetic composition. The mixing may be carried out with or without heating or cooling the ingredients. Particulates and other ingredients that are to be dispersed are then added with mixing to form a homogeneous mixture.

One embodiment of the present invention provides a method of improving curl of keratinous materials. The mascara composition described above is applied onto the keratinous materials. The keratinous materials are preferably keratin fibers, in particular eyelashes and eyebrows, but especially eyelashes. The mascara composition is applied onto the keratinous materials in an amount sufficient to improve the curl of the keratinous materials. To improve the curl of keratin fibers, the mascara composition may be applied onto the keratin fibers in an amount sufficient to increase the curl, and also a volume and/or length of the keratin fibers. The mascara is applied to a portion of keratinous surface that one desires to adopt a concave curvature, such as the top surface of the upper eyelash and allowed to dry. Accordingly, the mascara compositions may be brushed or applied onto the eyelashes with attentiveness to apply it predominantly on the top surface of the top eyelashes rather than the bottom surface of the top eyelashes.

The way by which the mascara composition is applied onto the keratinous materials is not limited. Preferably, the mascara composition is applied onto keratin fibers by a brush, a wand, or a comb.

The compositions may be applied to eyelashes as needed, preferably once or twice daily, more preferably once daily and then preferably allowed to dry before subjecting to contact such as with clothing or other objects.

Notwithstanding that the numerical ranges and parameters setting forth the broad scope of the invention are approximations, the numerical values set forth in the specific examples are reported as precisely as possible. Any numerical value, however, inherently contain errors necessarily resulting from the standard deviation found in their respective measurements.

The inventors have found that mascara compositions of the present invention have improved self-curling and also may be reduced in 'complexity.' In certain embodiments, no wax or oils are used and in certain other embodiments one polymer (the vinylpyrrolidone homopolymer) is used.

Examples Mascara Compositions

Mascara compositions of Example 1 and Comparative Example 1 were prepared by dissolving 20% by weight of PVP K-90 (vinylpyrrolidone homopolymer) in water and/or adding 20% by weight of one or various acrylic polymers, as indicated in Table 1 below. These percentages are on an actives basis.

The following SELF-CURLING TEST was performed on the various compositions. Using a flat iron, hair fiber strands (fake eyelashes), 12 mm in length secured between metal plates—available from SP Equation of Pourcieux, France—were straightened by gently stroking them using a commercially available hair straightener set to 450° F. for a sufficient period to straighten the fibers. Using a tongue depressor, various compositions to be tested were applied to the fake eyelashes and stroked ten times on one side of the simulated eyelashes. This deposits approximately 2 mg to 10 mg of composition. The treated lashes were put into a humidity chamber (25% RH and 32° C.) for 5 minutes. A curl measurement was then taken by placing a protractor near the eyelashes and visually estimating the angle of curl relative to the horizontal surface of the metal plate within which the fake eyelashes are secured.

The result was recorded as Initial Curl. The sample was then placed into a second humidity chamber (60% RH 32 C) for twenty minutes and another assessment was made of the curl as described above. The result was recorded as Curl Retention. The results, shown below indicate that mascara compositions including a high molecular weight vinylpyrrolidone homopolymer and an acrylic polymer having a glass transition temperature of 65° C. or more have surprisingly enhanced self-curling properties.

TABLE 1

| Ref. | Polymer(s) | Baseline (°) | Initial Curl (°) | Curl Retention (°) |
|---|---|---|---|---|
| Example 1 | PVP K-90[1] | 0 | 0-10 | 0 |
| Example 2 | LUVIMER MAE[2] | 0 | 10 | 0-10 |
| Example 3 | LUVISET SOFT[3] | 0-5 | 0-5 | 0 12 |
| Example 4 | FIXATE SUPERHOLD[4] | 0 | 0 | 0 |
| Example 5 | LUVISET SHAPE[5] | 0 | 45-90 | 45-90 |
| Example 6 | LUVISET ONE[6] | 0 | 10-20 | 10-20 |
| Example 7 | PVP K-90[1] + LUVIMER MAE[2] | 0 | 10-30 | 0-5 |
| Example 8 | PVP K-90[1] + LUVISET SOFT[3] | 0 | 0-20 | 0-10 |
| Example 9 | PVP K-90[1] + FIXATE SUPERHOLD[4] | 0 | 5-20 | 0-10 |
| Example 10 | PVP K-90[1] + LUVISET SHAPE[5] | 0-5 | 20-50 | 0-15 |
| Example 11 | PVP K-90[1] + LUVISET ONE[6] | 0 | 10-30 | 0-5 |

[1]PVP K-90, polyvinylpyrrolidone, available from Ashland Inc. of Kovington, KY.
[2]LUVIMER MAE, methacrylic acid/ethyl acrylate copolymer, available from BASF of Ludwigshafen, Germany.
[3]LUVIFLEX Soft, methacrylic acid/ethyl acrylate copolymer, available from BASF of Ludwigshafen, Germany
[4]FIXATE Superhold, alkyl(meth)acrylate/(meth)acrylic acid, available from Lubrizol Corporation of Wickliffe, Ohio
[5]LUVISET SHAPE, methyl methacrylate/methacrylic acid/urethane acrylate, available from BASF of Ludwigshafen, Germany
[6]LUVISET ONE, acrylate/methacrylamide copolymer, available from BASF of Ludwigshafen, Germany

What is claimed is:

1. A mascara composition consisting essentially of:
   a vehicle comprising water;
   a film-forming polymer portion consisting of a high molecular weight vinylpyrrolidone homopolymer, and an acrylic polymer having a glass transition temperature of 65° C. or more,
   wherein the high molecular weight vinylpyrrolidone homopolymer is present in a concentration of at least 10 percent by weight of the mascara composition,
   wherein the film-forming portion is stabilized in the vehicle,
   wherein the mascara composition is substantially free of wax, substantially free of oil, and substantially free of glycols, and
   wherein the mascara composition is self-curling as to induce curling of eyelashes upon drying with the use of an applicator for curling eyelashes.

2. The mascara composition of claim 1 wherein the high molecular weight vinylpyrrolidone homopolymer is present in a concentration by weight that is from about 10 percent to about 40 percent.

3. The mascara composition of claim 1 wherein the acrylic polymer having a glass transition temperature of 65° C. or more comprises one or more monomers selected from a group consisting of acrylic acid, methacrylic acid, acrylamide, methacrylamide, alkyl acrylates, alkyl methacrylates, and styrene.

4. The mascara composition of claim 1 wherein the acrylic polymer having a glass transition temperature of 65° C. or more consists of one or more monomers selected from a group consisting of acrylic acid, methacrylic acid, alkyl acrylates, and alkyl methacrylates.

5. The mascara composition of claim 1 wherein the acrylic polymer having a glass transition temperature of 65° C. or more is present in a concentration by weight that is from about 5 percent to about 30 percent.

6. The mascara composition of claim 1 wherein the high molecular weight vinylpyrrolidone homopolymer has a weight average molecular weight of 200,000 daltons or more.

7. The mascara composition of claim 1 wherein the high molecular weight vinylpyrrolidone homopolymer has a weight average molecular weight of 400,000 daltons or more.

8. The mascara composition of claim 1 wherein the acrylic polymer having a glass transition temperature of 65° C. or more has a glass transition temperature of 90° C. or more.

9. A method of applying makeup to the eyelashes, comprising applying directly to a top surface of eyelashes the mascara composition of claim 1.

10. The mascara composition of claim 1 wherein the wax is present in an amount of less than about 0.25% by weight of the mascara composition and the oil is present in an amount of less than about 0.25% by weight of the mascara composition.

11. The mascara composition of claim 1 which is free of wax and oil.

12. The mascara composition of claim 1 wherein the water is present in an amount of at least about 30% by weight of of the mascara composition.

13. The mascara composition of claim 1 wherein the acrylic polymer having a glass transition temperature of 65° C. or more is one or more selected from the group consisting of a methacrylic acid/ethyl acrylate copolymer, alkyl(meth)acrylate/(meth)acrylic acid copolymer, a methyl methacrylate/methacrylic acid/urethane acrylate copolymer, and an acrylate/methacrylamide copolymer.

14. The mascara composition of claim 13 wherein the acrylic polymer having a glass transition temperature of 65° C. or more is a methacrylic acid/ethyl acrylate copolymer.

15. The mascara composition of claim 13 wherein the acrylic polymer having a glass transition temperature of 65° C. or more is an alkyl(meth)acrylate/(meth)acrylic acid copolymer.

16. The mascara composition of claim 13 wherein the acrylic polymer having a glass transition temperature of 65° C. or more is a methyl methacrylate/methacrylic acid/urethane acrylate copolymer.

17. The mascara composition of claim 13 wherein the acrylic polymer having a glass transition temperature of 65° C. or more is an acrylate/methacrylamide copolymer.

* * * * *